US00PP23453P2

(12) United States Plant Patent
Nishikawa

(10) Patent No.: US PP23,453 P2
(45) Date of Patent: Mar. 5, 2013

(54) ***DELOSPERMA* PLANT NAMED 'JEWEL OF DESERT RUBY'**

(50) Latin Name: *Delosperma cooperi*
Varietal Denomination: Jewel of Desert Ruby

(75) Inventor: Koichiro Nishikawa, Quito (EC)

(73) Assignee: Ron Van Dijk Consultancy B.V., Boskoop (NL)

( * ) Notice: Subject to any disclaimer, the term of this patent is extended or adjusted under 35 U.S.C. 154(b) by 0 days.

(21) Appl. No.: 13/199,812

(22) Filed: Sep. 9, 2011

(51) Int. Cl.
*A01H 5/00* (2006.01)

(52) U.S. Cl. ..... Plt./422

(58) Field of Classification Search ..... Plt./422, Plt./263.1
See application file for complete search history.

*Primary Examiner* — Howard Locker
(74) *Attorney, Agent, or Firm* — Penny J. Aguirre

(57) ABSTRACT

A new cultivar of *Delosperma* plant, 'Jewel of Desert Ruby', characterized by its compact and very horizontal plant habit, its relatively small leaves, its very floriferous and long blooming flowering habit, and its flowers that are deep red in color with white centers and yellow anthers.

2 Drawing Sheets

Botanical classification: *Delosperma cooperi.*
Variety denomination: 'Jewel of Desert Ruby'.

CROSS REFERENCE TO RELATED APPLICATIONS

This application is co-pending with U.S. Plant Patent Applications filed for plants derived from the same breeding program that are entitled *Delosperma* Plant Named 'Jewel of Desert Rosequartz' (U.S. Plant patent application Ser. No. 13/199,787), *Delosperma* Plant Named 'Jewel of Desert Moon Stone' (U.S. Plant patent application Ser. No. 13/199,823), *Delosperma* Plant Named 'Jewel of Desert Topaz' (U.S. Plant patent application Ser. No. 13/199,826), *Delosperma* Plant Named 'Jewel of Desert Peridot' (U.S. Plant patent application Ser. No. 13/199,815), and *Delosperma* Plant Named 'Jewel of Desert Garnet' (U.S. Plant patent application Ser. No. 13/199,846).

BACKGROUND OF THE INVENTION

The present invention relates to a new and distinct cultivar of *Delosperma* plant, botanically known as *Delosperma cooperi* 'Jewel of Desert Ruby' and will be referred to hereinafter by its cultivar name, 'Jewel of Desert Ruby'. The new cultivar of *Delosperma* is a herbaceous perennial grown for container and landscape use.

The new cultivar was derived from a controlled breeding program conducted by the Inventor in Ichinimiya-City, Aichi-Pref, Japan. The overall purpose of the breeding program was to develop new cultivars of *Delosperma* plants with low-growing and well-spreading growth habits combined with long flowering periods and a unique range of flower colors.

'Jewel of Desert Ruby' was selected in the Inventor's trial garden in November 2006 as a single unique plant from amongst the seedlings derived from self-crossing an unnamed plant from the Inventor's breeding program in 2005. The Inventor's reference number for the parent plant is 2005-1.

Asexual propagation of the new cultivar was first accomplished by softwood cuttings in 2009 by the Inventor in Ichinimiya-City, Aichi-Pref, Japan. Propagation by softwood cuttings has shown that the unique features of the new cultivar are stable and reproduced true to type in successive generations.

SUMMARY OF THE INVENTION

The following traits have been repeatedly observed and are determined to be the characteristics of the new cultivar. These attributes in combination distinguish 'Jewel of Desert Ruby' as a unique cultivar of *Delosperma.*

1. 'Jewel of Desert Ruby' exhibits a compact and very horizontal plant habit.
2. 'Jewel of Desert Ruby' exhibits relatively small leaves.
3. 'Jewel of Desert Ruby' exhibits a very floriferous and long blooming flowering habit.
4. 'Jewel of Desert Ruby' exhibits flowers that are red in color with deep pink and white centers and yellow anthers.

The parent plant of 'Jewel of Desert Ruby', Ref. No. 2005-1, differs from 'Jewel of Desert Ruby' in having a more upright (less horizontal) plant habit, in blooming for a shorter time period, and in having flowers that are pink in color and lack white centers. 'Jewel of Desert Ruby' can be most closely compared to the cultivar 'Jewel of Desert Rosequartz', which is similar to 'Jewel of Desert Ruby' in having a horizontal plant habit. 'Jewel of Desert Rosequartz' differs from 'Jewel of Desert Ruby' in having a less regular plant habit, in having flowers that are light pink in color with white centers and yellow anthers, and in being more heat tolerant.

'Jewel of Desert Ruby' can also be compared to cultivars with co-pending patent applications from the same breeding program that differ from 'Jewel of Desert Ruby' most significantly in flower color:

'Jewel of Desert Moon Stone' has white flowers with yellow anthers.

'Jewel of Desert Topaz' has yellow-orange flowers with red petal tips, white-light purple centers, and yellow anthers.

'Jewel of Desert Peridot' has yellow flowers with white centers and yellow anthers.

'Jewel of Desert Garnet' has red-orange flowers with pink centers and yellow anthers.

BRIEF DESCRIPTION OF THE DRAWINGS

The accompanying colored photographs illustrate the overall appearance and distinct characteristics of the new *Delosperma*. The plant in the photograph is 3 months in age as grown in a 7-cm container in a unheated greenhouse in Noordwijkerhout, The Netherlands.

The photograph in FIG. 1 provides a side view of 'Jewel of Desert Ruby' in bloom.

Figure 1:
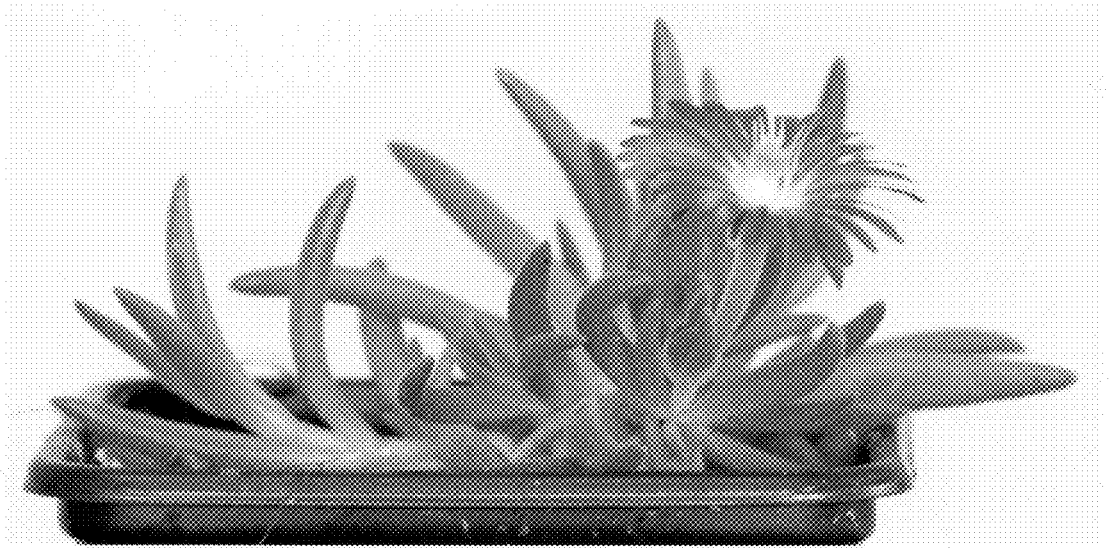
Figure 2:
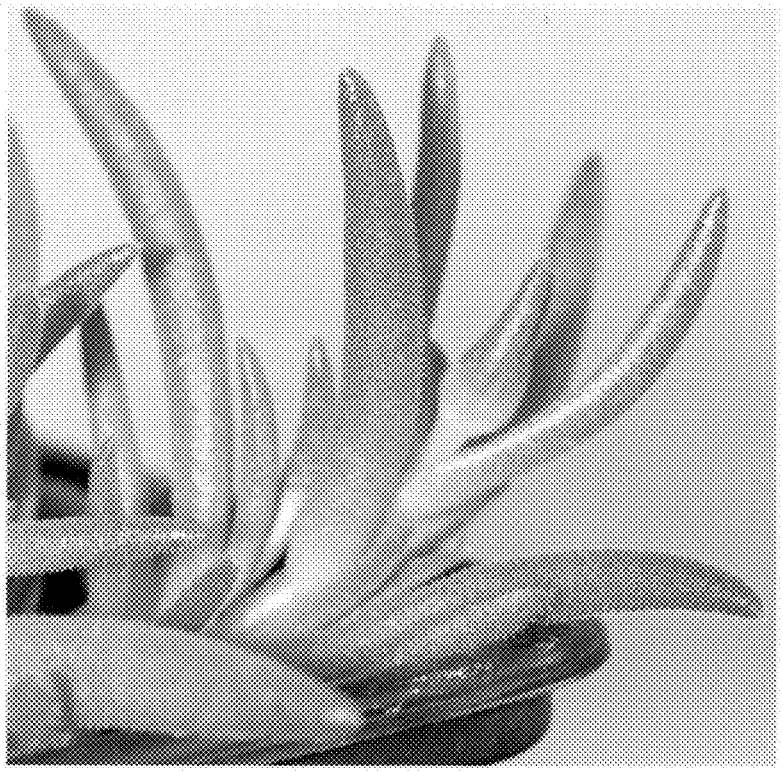

The photograph in FIG. 2 provides a close-up view of the foliage of 'Jewel of Desert Ruby'.

Figure 3:
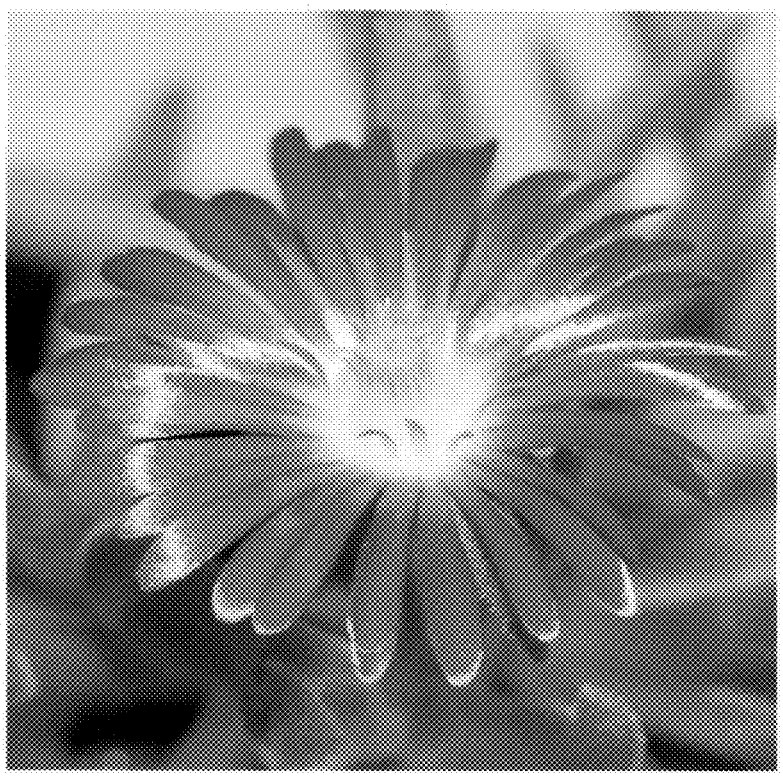

The photograph in FIG. 3 provides a close-up view of a flower of 'Jewel of Desert Ruby'.

The colors in the photographs may differ slightly from the color values cited in the detailed botanical description, which accurately describe the colors of the new *Delosperma*.

DETAILED BOTANICAL DESCRIPTION

The following is a detailed description of three month-old plants of the new cultivar as grown in 7-cm containers in a unheated greenhouse in Noordwijkerhout, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Mid April to mid September in Noordwijkerhout, The Netherlands.

*Plant type*.—Herbaceous perennial.

*Plant habit*.—Compact, About 5 cm in height and about 9 cm in diameter, with mature plants reaching up to 10 cm in height and 30 cm in spread.

*Cold hardiness*.—Observed to be hardy to U.S.D.A. Zone 7.

*Diseases*.—No more susceptible or resistant to diseases than other *Delosperma cooperi* varieties, diseases are typically not a problem for *Delosperma cooperi*, except when grown with too much moisture.

*Root description*.—Fibrous roots.

*Propagation*.—Softwood cuttings.

*Growth habit*.—Moderately vigorous.

Stem description:

*Shape*.—Round.

*Stem color*.—145C with older stems 153D.

*Stem size*.—Lateral branches; an average of 2.7 cm in length and 2 mm in diameter.

*Internode length*.—An average of 5 mm.

*Stem substance*.—Succulent.

*Stem surface*.—Moderately glossy, sparsely to moderately pubescent with very short glandular hairs; an average of 0.2 mm in length and about 155C in color.

*Branching habit*.—Basal branching with an average of 4 lateral branches per stem.

Foliage description:

*Leaf shape*.—Ligulate, triangular in diameter.

*Leaf substance*.—Succulent.

*Leaf division*.—Simple.

*Leaf base*.—Cuneate.

*Leaf apex*.—Acute.

*Leaf venation*.—No veins visible.

*Leaf margins*.—Entire.

*Leaf arrangement*.—Opposite.

*Leaf surface* (*Upper and lower surface*).—Slightly glossy, slightly pubescent with very short glandular hairs; an average of 0.2 mm in length, 155C in color.

*Leaf color*.—Young upper and lower surface; 143A, base 144B, mature upper and lower surface; 137B.

*Leaf size*.—About 3.5 cm in length and 4.5 mm in width.

*Leaf quantity*.—Average of 10 per lateral branch.

*Leaf attachment*.—Sessile.

Inflorescence description:

*Inflorescence type*.—Flowers solitary.

*Flower number*.—An average of 4 per lateral stem, 12 per plant in a 7-cm container.

*Flower fragrance*.—None.

*Flower aspect*.—Outward to upright.

*Flower longevity*.—A few days.

*Flower type*.—Single.

*Flower size*.—Average of 2.7 cm in diameter and 1.0 cm in depth.

*Flower buds*.—Broadly ovate to oblong in shape, an average of 1.1 cm in length and 6 mm in diameter, color; 145A with tip 143A.

*Calyx*.—Rotate in shape, average of 5 mm in depth and 1.5 cm in diameter.

*Sepals*.—5, ovate in shape, margin entire, an average of 8 mm in length and 3 mm in width, broadly acute apex, broadly cuneate base, surface is smooth and dull, color: young upper and lower surface; 145A fading to 143A, mature upper surface; 143A, mature lower surface; 145A fading to 143A.

*Petals*.—An average of 30 per flower, rotate and slightly reflexed, narrowly oblanceolate in shape, surface is smooth and glossy on both surfaces, margin entire, apex obtuse, base cuneate, an average of 1.3 cm in length and 2 mm in width, color: opening flowers and fully opened upper surface; 45A, base N74A blending into 155A at very base, opening flowers and fully opened lower surface; 61A to 61B, base N74A blending into 155A at very base, fading upper surface; 47C, base N74C blending into 155A at very base, fading lower surface; 61C, base N74A blending into 155A at very base.

*Petaloids*.—An average of 30 per flower, rotate and near vertical surrounding stamens, lanceolate in shape, surface is smooth and dull on both surfaces, margin entire, apex attenuate, base truncate, an average of 1.3 cm in length and 2 cm in width, color: opening flowers and fully opened upper surface; 45A, base N74A blending into 155A at very base, opening flowers and fully opened lower surface; 61A to 61B, base N74A blending into 155A at very base; fading upper surface; 47C, base N74C blending into 155A at very base, fading lower surface; 61C, base N74A blending into 155A at very base.

*Peduncle*.—Average of 2.4 cm in length and 1.5 mm in diameter, weak in strength, straight on top of lateral branch at 0°, 148A and 148B in color, surface moderately glossy, sparsely to moderately pubescent with very short glandular hairs.

Reproductive organs:

*Pistils*.—About 5, an average of 2 mm in length, triangular shaped stigma, style and stigma (not distinguishable) are an average of 2 mm in length and 144A in color, ovary is 143C in color.

*Stamens*.—Average 60, anthers are dorsifixed, narrowly oblong in shape, an average of 0.5 mm in diameter and 2 mm in length, filaments are 155D in color, anther is 13A to 13B in color, pollen is moderate in quantity and 14A to 14B in color.

*Fruit*.—Fruit and seed production was not observed under the conditions tested.

It is claimed:

1. A new and distinct variety of *Delosperma* plant named 'Jewel of Desert Ruby' as described and illustrated herein.

* * * * *